(12) United States Patent
Dunko

(10) Patent No.: US 7,693,535 B2
(45) Date of Patent: Apr. 6, 2010

(54) COMMUNICATION SYSTEMS AND METHODS FOR PROVIDING A GROUP PLAY LIST FOR MULTIMEDIA CONTENT RECORDS

(75) Inventor: Gregory Dunko, Cary, NC (US)

(73) Assignee: Sony Ericsson Mobile Communications AB, Lund (SE)

( * ) Notice: Subject to any disclaimer, the term of this patent is extended or adjusted under 35 U.S.C. 154(b) by 643 days.

(21) Appl. No.: 11/644,135

(22) Filed: Dec. 22, 2006

(65) Prior Publication Data
US 2008/0154959 A1    Jun. 26, 2008

(51) Int. Cl.
*H04Q 7/20* (2006.01)

(52) U.S. Cl. ............... 455/518; 455/519; 455/426.1; 455/412.1; 455/550.1; 455/414.1; 709/202; 709/203; 709/207; 709/219; 709/218

(58) Field of Classification Search ............... 455/518, 455/519, 500, 517, 466, 550.1, 412.1, 412.2, 455/426.1, 426.2, 414.1–414.4, 456.1–457, 455/566, 3.01–3.06; 707/10, 104.1; 709/202, 709/203, 207, 219, 218
See application file for complete search history.

(56) References Cited

U.S. PATENT DOCUMENTS

| | | | |
|---|---|---|---|
| 6,856,990 B2* | 2/2005 | Barile et al. .............. | 707/10 |
| 2003/2227478 | 12/2003 | Chatfield ................. | 345/751 |
| 2004/0003090 A1 | 1/2004 | Deeds ..................... | 709/227 |
| 2006/0031368 A1* | 2/2006 | deCone .................. | 709/207 |
| 2006/0084456 A1 | 4/2006 | Dunko et al. ............ | 455/419 |
| 2006/0179078 A1* | 8/2006 | McLean ................ | 707/104.1 |
| 2006/0265349 A1 | 11/2006 | Hicken .................. | 707/1 |
| 2007/0150444 A1* | 6/2007 | Chesnais et al. .......... | 707/3 |
| 2007/0264982 A1* | 11/2007 | Nguyen et al. .......... | 455/414.1 |
| 2008/0091771 A1* | 4/2008 | Allen et al. .............. | 709/203 |

FOREIGN PATENT DOCUMENTS

EP    1 515 340    3/2005

OTHER PUBLICATIONS

International Search Report and Written Opinion for PCT Application PCT/US2007/015817 mailed Jan. 24, 2008.

* cited by examiner

*Primary Examiner*—Keith T Ferguson
(74) *Attorney, Agent, or Firm*—Myers Bigel Sibley & Sajovec

(57) ABSTRACT

Methods for providing a group play list for a plurality of multimedia content records include associating respective ones of a plurality of users associated with a user network with corresponding ones of the multimedia content records on the group play list. A presence status of the respective ones of the users associated with the user network is detected. Rendering of the multimedia content records on the group play list to the users associated with the network is automatically adjusted based on the detected presence status. The user network may be, for example, a computer based social network.

20 Claims, 4 Drawing Sheets

COMMUNICATION SYSTEMS AND METHODS FOR PROVIDING A GROUP PLAY LIST FOR MULTIMEDIA CONTENT RECORDS

FIELD OF THE INVENTION

The present invention relates to electronic devices and, more particularly, to electronic devices, methods and computer program products for playing multimedia content records, such as audio files, video files, and/or image files.

BACKGROUND

Electronic devices, such as wireless communication terminals (e.g., cellular telephones), are widely used to store and play back digital audio files. In addition, electronic devices may be used to store other types of multimedia files, such as digital image files and/or digital video files. Multimedia files may include any other type of file containing audio, visual or textual information. For example, as used herein, a "multimedia" file may include MMS or PPT message files in addition to or in place of typical multimedia files, such as audio, image and/or video files.

Digital audio files are typically stored in a compressed digital format, such as MP3, AIFF and/or other digital formats. Due to the limited amount of power available to mobile electronic devices, digital audio files are typically played back at a low power level via personal headphones and/or un-powered speakers which may permit only one, or a relatively few, people to listen to the audio file. Powered, amplified speakers and docking stations may be used to play audio files at higher power levels. However, such devices may be suitable only for particular hardware interfaces and/or may still be useful only for limited numbers of listeners.

Some mobile electronic devices include video screens and associated driving circuitry capable of displaying/playing digital image files and/or digital video files. However, due to the typical requirements of small size, low power and/or portability, mobile electronic devices typically include small video screens that may be suitable for viewing only by a single person, or at most very few people.

Processor-based electronic computing devices are also being used more frequently to support computer-based social networking groups, such as MySpace and Facebook. In such user-based social networks, users who are group members may exchange communications and the like with other group members.

Other types of network applications have been developed to facilitate sharing of play lists and the like for multimedia files. For example, a music recommendation system allowing sharing of play lists has been proposed.

SUMMARY

In some embodiments of the present invention, methods for providing a group play list for a plurality of multimedia content records include associating respective ones of a plurality of users associated with a user network with corresponding ones of the multimedia content records on the group play list. A presence status of the respective ones of the users associated with the user network is detected. Rendering of the multimedia content records on the group play list to the users associated with the network is automatically adjusted based on the detected presence status. The user network may be, for example, a computer based social network.

In further embodiments, automatically adjusting rendering includes skipping rendering of a multimedia content record on the group play list associated with one of the respective ones of the users having a presence status indicating the one of the respective ones of the users is not present on the user network. An indication of the presence status of one of the not present user may be provided while rendering a multimedia content record on the group play list associated with the not present user.

In other embodiments, the users are associated with respective communication terminals. The methods further include identifying a respective one of the users associated with one of the multimedia content records that is currently being rendered as an active user. A request is received from a requesting one of the users to communicate with the active user. A communication connection is automatically established between respective ones of the communication terminals associated with the active user and the requesting user responsive to the received request. Receiving a request may be preceded by configuring the communication terminal of the requesting user to communicate with the communication terminal of the active user responsive to identifying the active user. The communication terminals associated with the requesting user and the active user may be wireless mobile terminals and the communication connection may be a push to talk (PTT) communication connection. Receiving the requesting may include detecting selection of a PTT feature of the requesting user. Automatically establishing the communication connection may include prioritizing an identification of the active user in a contact list associated with the PTT feature. Prioritizing the identification may include placing the identification at a top of the contact list.

In further embodiments, the communication connection includes a text message transmission. Automatically establishing the communication connection includes prioritizing an identification of the active user in a contact list associated with a text message feature of the communication terminal of the requesting user.

In other embodiments, ones of the multimedia content records are associated with respective slots on the group play list. The slots on the group play list are associated with corresponding ones of the users. Associating respective ones of the users may include receiving an identification of the multimedia content record to be associated with respective slots on the group play list from the corresponding ones of the users. Receiving an identification may include receiving the multimedia content record. Receiving an identification may include receiving a designation of a storage device and/or storage address from which the multimedia content record can be retrieved for rendering.

In yet further embodiments, associating respective ones of the users further includes receiving a plurality of identifications of multimedia content records to be associated with a single slot of the group play list from the corresponding one of the users. Each of the plurality of identifications has an associated user state. Automatically adjusting rendering further includes detecting a current state associated with a respective one of the users associated with the single slot of the group play list. One of the plurality of the identifications received for the single slot is selected as corresponding to the multimedia content record to be rendered for the single slot based on a comparison of the detected current state of the respective one of the users and the associated user state of the plurality of identifications.

In other embodiments, methods of rendering a group play list including a plurality of multimedia content records are provided. The group play list is associated with a computer based social network. The methods include identifying an active user associated with the social network as corresponding with one of the multimedia content records on the group play list. A presence status of the active user is detected. Rendering of the multimedia content records on the group play list is automatically adjusted based on the detected presence status. Detecting the presence status may include detecting that the active user is not present on the social network and automatically adjusting rendering may include skipping rendering of the one of the multimedia content records responsive to detecting that the active user is not present on the social network. Detecting the presence status may include detecting that the active user is present on the social network and automatically adjusting rendering may include rendering the one of the multimedia content records responsive to detecting that the active user is present on the social network. The methods may further include receiving a request to communicate while rendering the one of the multimedia records and automatically establishing a communication connection to the active user responsive to the received request.

In yet further embodiments, systems for rendering a group play list including a plurality of multimedia content records are provided. The group play list is associated with a computer based social network. The systems include a generation module, a presence detection module and a rendering module. The generation module generates the group play list including associating respective ones of a plurality of users associated with the social network with corresponding ones of the multimedia content records on the group play list. The presence detection module detects a presence status of the respective ones of the users on the social network. The rendering module renders the multimedia content records on the group play list to the users associated with the social network based on the detected presence status of the respective users, including adjusting rendering of a current record of the group play list responsive to detecting that an active one of the users associated with the current record is not present on the social network. The systems may further include a communication module that automatically establishes a communication connection between respective communication terminals associated with the active one of the users and a requesting one of the users responsive to a request received while rendering a multimedia content record associated with the current record.

DETAILED DESCRIPTION OF EMBODIMENTS OF THE INVENTION

Figure 1:
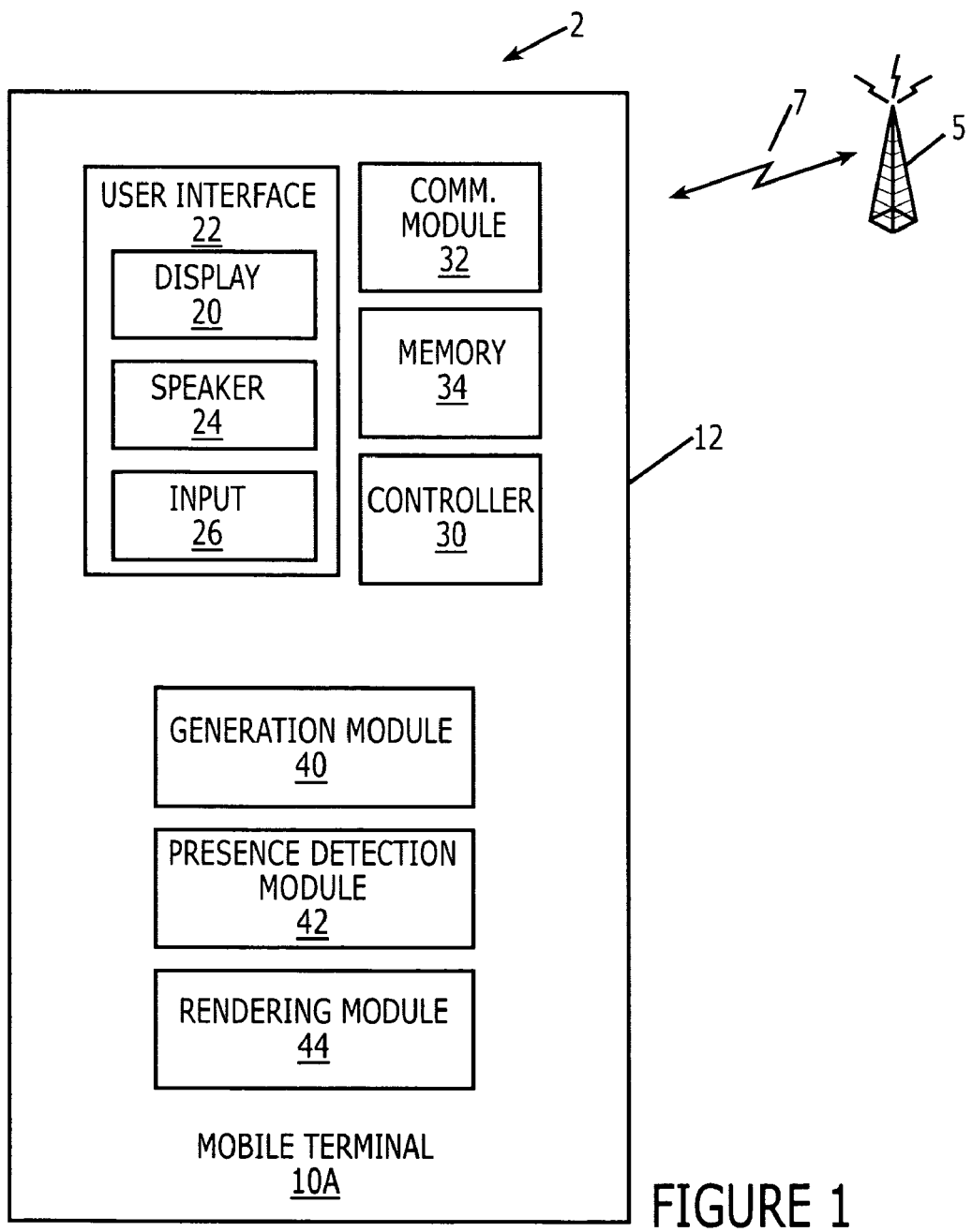
FIG. 1 is a schematic diagram of a mobile wireless communication terminal according to some embodiments of the present invention and an exemplary base station transceiver.

The present invention now will be described more fully with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art. Like numbers refer to like elements throughout.

As used herein, the term "comprising" or "comprises" is open-ended, and includes one or more stated features, integers, elements, steps, components or functions but does not preclude the presence or addition of one or more other features, integers, elements, steps, components, functions or groups thereof.

As used herein, the term "and/or" includes any and all combinations of one or more of the associated listed items.

As used herein, the common abbreviation "e.g.", which derives from the Latin phrase "exempli gratia," may be used to introduce or specify a general example or examples of a previously mentioned item, and is not intended to be limiting of such item. If used herein, the common abbreviation "i.e.", which derives from the Latin phrase "id est," may be used to specify a particular item from a more general recitation.

The terminology used herein is for the purpose of describing particular embodiments only and is not intended to be limiting of the invention. As used herein, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. Furthermore, "coupled" or "connected" as used herein may include wirelessly coupled or connected.

Well-known functions or constructions may not be described in detail for brevity and/or clarity.

The present invention may be embodied as methods, electronic devices, and/or computer program products. Accordingly, the present invention may be embodied in hardware and/or in software (including firmware, resident software, micro-code, etc.), which may be generally referred to herein as a "circuit" or "module". Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

Embodiments according to the present invention are described with reference to block diagrams and/or operational illustrations of methods and communication terminals. In this regard, each block may represent a module, segment, or portion of code, which comprises one or more executable instructions for implementing the specified logical function (s). It is to be understood that each block of the block diagrams and/or operational illustrations, and combinations of blocks in the block diagrams and/or operational illustrations, can be implemented by radio frequency, analog and/or digital hardware, and/or program instructions. These program instructions may be provided to a controller, which may include one or more general purpose processors, special purpose processors, ASICs, and/or other programmable data processing apparatus, such that the instructions, which execute via the controller and/or other programmable data processing apparatus, create means for implementing the functions/acts specified in the block diagrams and/or operational block or blocks. In some alternate implementations, the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

These computer program instructions may also be stored in a computer-usable or computer-readable memory that may direct a computer or other programmable data processing apparatus to function in a particular manner, such that the instructions stored in the computer usable or computer-readable memory produce an article of manufacture including instructions that implement the function specified in the flowchart and/or block diagram block or blocks.

The computer-usable or computer-readable medium may be, for example but not limited to, an electronic, magnetic, optical, electromagnetic, infrared, or semiconductor system, apparatus, or device. More specific examples (a nonexhaustive list) of the computer-readable medium include the following: hard disks, optical storage devices, magnetic storage devices, a portable computer diskette, a random access memory (RAM), a read-only memory (ROM), an erasable programmable read-only memory (EPROM or Flash memory), and a compact disc read-only memory (CD-ROM).

As used herein, "electronic component" means an active device as contrasted with a passive electrical connector or the like. An electronic component may include a processor.

As used herein, "streamed" or "streaming" means that a file, such as an audio or song file, is continuously sent via a digital signal to a receiving device where the audio or song file is concurrently played via a suitable receiving application. The digital signal is typically buffered.

As used herein, a "communication terminal" includes, but is not limited to, a terminal that is configured to receive/transmit communication signals via a wireline connection, such as via a public-switched telephone network (PSTN), digital subscriber line (DSL), digital cable, or another data connection/network, and/or via a wireless interface with, for example, a cellular network, a satellite network, a wireless local area network (WLAN), and/or another communication terminal.

When the communication terminal is configured to communicate over a wireless interface, it is referred to herein as a "wireless communication terminal" or a "wireless terminal." Examples of wireless terminals include, but are not limited to, a cellular telephone, personal data assistant (PDA), pager, and/or a computer that is configured to communicate data over a wireless communication interface that can include a cellular telephone interface, a Bluetooth interface, a wireless local area network interface (e.g., 802.11), another RF communication interface, and/or an optical/infra-red communication interface.

As used herein, "mobile terminals" may be portable, transportable, installed in a vehicle (aeronautical, maritime, or land-based), or situated and/or configured to operate locally and/or in a distributed fashion at any other location(s) on earth and/or in space.

As used herein "play" and "playback" and "render" and "rendering" of a multimedia file is used in a general sense and may include playing an audio file over a speaker, displaying a digital image on a display screen and/or displaying a video file on a display screen and/or simultaneously playing an audio file associated with and/or embedded in the video file over a speaker.

Some embodiments of the present invention will now be described below with respect to FIGS. 1-5. Some embodiments of the present invention provide host center devices capable of managing and rendering multimedia files identified on a multimedia file play list including one or more multimedia file identifications. The multimedia files may be maintained by the host center device and/or may retrieved from a remote location, such as from one or more remotely located wireless communication terminals, which devices may be associated with users (members) of a social network supported by the host device and/or by the host device in combination with a server or servers supporting additional aspects of the social network. The host device may itself be a wireless communication terminal. Furthermore, the host device may be configured to permit automatic and/or manual prioritization of multimedia files in the multimedia file play list. The multimedia files may be played back at the host device and/or on a media center device associated with the host device. The multimedia files may be played back by communication devices and/or media center devices associated with some and/or all of the communication devices associated with the members of the social network.

Referring now to FIG. 1, an exemplary communication system, shown as mobile wireless communication terminal 10A, in accordance with some embodiments of the present invention is illustrated. It will be appreciated that although embodiments of the invention are illustrated in connection with a wireless communication terminal, the invention may include wired mobile and/or non-mobile communication terminals and methods. Furthermore, while aspects of a host device and a communication device associated with a member of a social group are both illustrated in FIG. 1, all such modules and/or circuits may not be found in some embodiments of the present invention. The wireless terminal 10A is configured to communicate data with one or more other wireless terminals over a direct wireless communication interface therebetween, over another wireless communication interface through one or more cellular base stations, and/or over another wireless communication interface through a wireless local area network (WLAN) router WiMax and/or other wireless network. It will further be understood that, while described for illustrative purposes with reference to wireless communications herein, the present invention is not limited to such embodiments and the communication between a host device and/or user communication devices may be a wired connection and/or a connection including both wired and wireless links supporting, for example, a packetized communication protocol, such as the Internet Protocol (IP).

The wireless terminal 10A may be a mobile radiotelephone forming a part of a radiotelephone communication system 2 as illustrated in FIG. 1. The system 2 includes the mobile wireless communication terminal 10A and a base station transceiver, which is part of a wireless communications network 5. In some embodiments of the present invention, the network 5 includes a base station transceiver that includes the radio transceiver(s) that define an individual cell in a cellular network and communicates with the mobile terminal 10A (via an interface 7) and other mobile terminals in the cell using a radio-link protocol. It will be understood that, in some embodiments of the present invention, many base station transceivers may be connected through, for example, a mobile switching center and other devices to define the wireless communications network 5.

The mobile terminal 10A in the illustrated embodiments includes a portable housing assembly 12, a controller 30, a communication module 32, and a memory 34. The mobile terminal 10A further includes a user interface 22 (i.e., a man machine interface) including a display 20, a speaker 24 (i.e., a sound transducer), and at least one input device 26. The foregoing components of the mobile terminal 10A may be included in many conventional mobile terminals and their functionality is generally known to those skilled in the art. The mobile terminal 10A further includes a generation module 40, a presence detection module 42 and a rendering module 44, which may be stored in the memory 34.

The display 20 may be any suitable display screen assembly. For example, the display 20 may be a liquid crystal display (LCD) with or without auxiliary lighting (e.g., a lighting panel). In some cases the mobile terminal 10A may be capable of playing video content of a particular quality. For example, a mobile terminal 10A may be configured to display a video stream having a particular aspect ratio, such as 16:9 or 4:3. A number of standard video formats have been proposed for mobile terminals, including Quarter VGA (QVGA, 320×240 pixels), Common Intermediate Format (CIF, 360×288 pixels) and Quarter Common Intermediate Format (QCIF, 180×144 pixels). Moreover, some mobile terminals may have multiple display screens having different display capabilities. Thus, a mobile terminal 10A may be capable of displaying video in one or more different display formats.

The user interface 22 may include any suitable input device(s) including, for example, a touch activated or touch sensitive device (e.g., a touch screen), a joystick, a keyboard/keypad, a dial, a directional key or keys, and/or a pointing device (such as a mouse, trackball, touch pad, etc.). The speaker 24 generates sound responsive to an input audio signal. The user interface 22 can also include a microphone coupled to an audio processor that is configured to generate an audio data stream responsive to sound incident on the microphone.

The controller 30 may support various functions of the wireless terminal 10A. The controller 30 can be any commercially available or custom microprocessor, for example. In use, the controller 30 of the wireless terminal 10A may generate a display image on the display 20. In some embodiments, however, a separate signal processor and/or video chip (not shown) may be provided in the wireless terminal 10A and may be configured to generate a display image on the display 20.

The memory 34 is configured to store digital information signals and data such as a digital multimedia files (e.g., digital audio, image and/or video files).

The communication module 32 is configured to communicate data over one or more wireless interfaces (e.g., wireless interfaces 7, 112, 114, 116, 122, and 134 as discussed herein (FIGS. 1 and 2)) to another remote wireless terminal as discussed herein. The communication module 32 can include a cellular communication module, a direct point-to-point connection module, and/or a WLAN module or other wireless network.

With a cellular communication module, the wireless terminal 10A can communicate via the base station(s) of the network 5 using one or more cellular communication protocols such as, for example, Advanced Mobile Phone Service (AMPS), ANSI-136, Global Standard for Mobile (GSM) communication, General Packet Radio Service (GPRS), enhanced data rates for GSM evolution (EDGE), code division multiple access (CDMA), wideband-CDMA, CDMA2000, and Universal Mobile Telecommunications System (UMTS). The cellular base stations may be connected to a Mobile Telephone Switching Office (MTSO) wireless network, which, in turn, can be connected to a PSTN and/or another network. Internet Protocol (IP) type data may further be routed for transmission over the Internet or world wide web using existing wired and wireless network components.

A direct point-to-point connection module may include a direct RF communication module or a direct IR communication module. The direct RF communication module may include a Bluetooth module. With a Bluetooth module, the wireless terminal 10A can communicate via an ad-hoc network through a direct point-to-point interface.

With a WLAN module, the wireless terminal 10A can communicate through a WLAN (e.g., a router 120 (FIG. 2)) using a communication protocol that may include, but is not limited to, 802.11a, 802.11b, 802.11e, 802.11g, and/or 802.11i.

The communication module 32 can include a transceiver typically having a transmitter circuit and a receiver circuit, which respectively transmit outgoing radio frequency signals (e.g., to the network 5, a router or directly to another terminal) and receive incoming radio frequency signals (e.g., from the network 5, a router or directly from another terminal), such as voice and data signals, via an antenna. The communication module 32 may include a short range transmitter and receiver, such as a Bluetooth transmitter and receiver. The antenna may be an embedded antenna, a retractable antenna or any antenna known to those having skill in the art without departing from the scope of the present invention. The radio frequency signals transmitted between the wireless terminal 10A and the network 5, router or other terminal may include both traffic and control signals (e.g., paging signals/messages for incoming calls), which are used to establish and maintain communication with another party or destination. The radio frequency signals may also include packet data information, such as, for example, cellular digital packet data (CDPD) information or general packet radio service (GPRS). In addition, the transceiver may include an infrared (IR) transceiver configured to transmit/receive infrared signals to/from other electronic devices via an IR port.

The wireless terminal 10A may also be configured to electrically couple with another terminal via a wireline or cable for the transmission of digital communication signals therebetween. The wireless terminal 10A may include further components, such as a camera device configured to generate a still image and/or video data stream based on incident light.

The generation module 40 in some embodiments generates a group play list, including associating respective ones of a plurality of users associated with the social network with corresponding ones of the multimedia content records on the group play list. Such an association is illustrated, for example, in FIG. 3 where the AC/DC song "Back In . . . " is associated with a submitting user "Martin." As also visually displayed in FIG. 3, the respective multimedia records may themselves be associated with respective slots on the group play list and the slots may be associated with corresponding ones of the users so as to provide the linkage between a multimedia record and a user. In other words, as will be further described herein, the group members may collectively create a group play list. The group play list may then be shared amongst members of the group, for example, so that they may all be able to listen to the same music (concurrently or at different times) with different contributions from different ones of the group members. For example, in a social network including member users, group members may have their own content that is available for sharing with other members. This content may be distributed amongst the users' devices, may be available on all the devices, or may be retrievable from a common site, such as a shared content server 127. In this way, a large library of group content may be provided that is accessible by some or all group members in the social network.

As a result of the association of group members with particular multimedia content or slots in the group play list containing content designated by such group members, other group members may further begin to associate certain songs with certain users based upon those users' selections in the group play list. For example a user "Matt" may always choose "Usher" songs in his song slot and group members may, over time, come to think of Matt when they hear the "Usher" songs.

Figure 3:
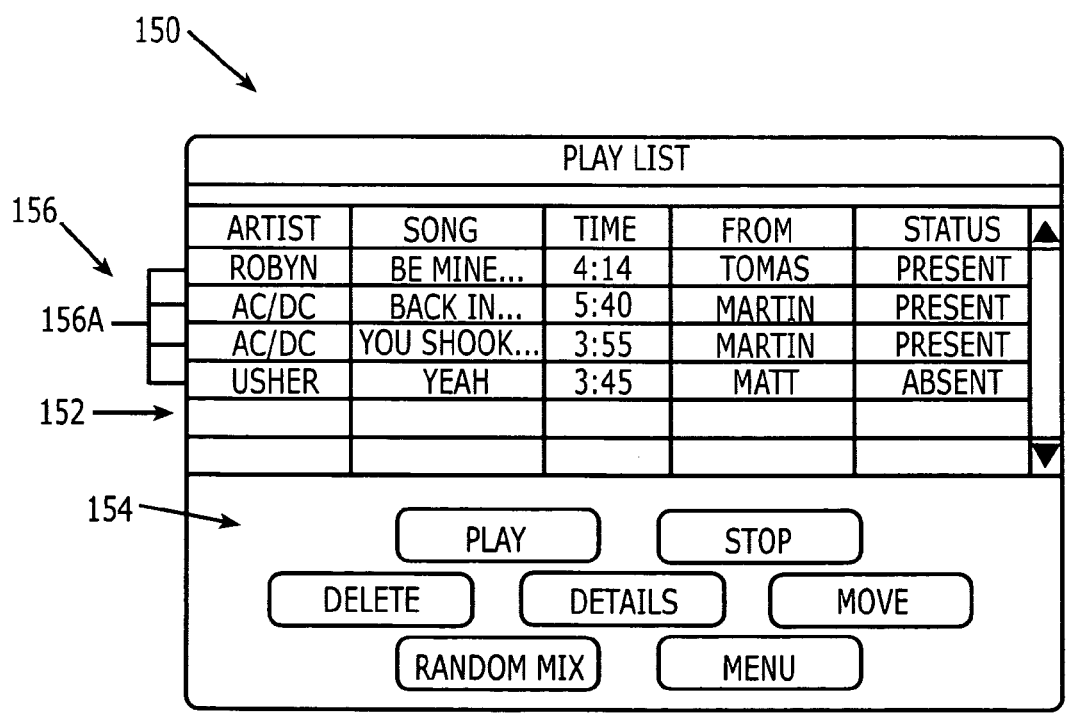
FIG. 3 is a schematic diagram illustrating a display of the mobile wireless communication terminal of FIG. 1 in accordance with some embodiments of the present invention.

The group play list, as illustrated in the example of FIG. 3, may consist of a variety of ordered "slots" that are associated with the respective group members. For example, every fourth song may be provided by a particular user "Ben." In some embodiments, a user, such as Ben, may choose different songs or "favorites" to associate with one or more of the assigned slots depending upon his mood or other state indication of the user associated with the slot. As such, the generation module 40 in some embodiments may be configured to generate a group play list that includes a plurality of different content records for an individual slot, where some discrete determinable user state indication may be used to select between the respective ones of a plurality of designated multimedia content records at the time of rendering of music or the like from the particular slot (i.e., when the slot including a plurality of optionally selectable records becomes first on a group play list).

In the illustrated embodiments of FIG. 1, the mobile terminal 10A further includes the presence detection module 42. The presence detection module 42 detects a presence status of the respective ones of the users on the social network. Such status information is illustrated, for example, in FIG. 3, where users "Thomas" and "Martin" are shown as present while user "Matt" is shown as absent. As will be described further herein, such presence information for a group member may be used in adjusting rendering of the group play list. For example, if a group member is not present when his or her selection in the play list comes up, then the rendering device may act accordingly. For example, the play list may "skip" the song that is due next on the play list. By way of further example, some indication or default may be provided that indicates that the associated group member is not currently available, which indication may be provided for display on communication devices associated with other group members of the social network, whether or not they are listening to the group play list at any given time.

Further shown in FIG. 1 is the rendering module 44. The rendering module 44 renders the multimedia content records on the group play list to the users associated with the social network based on the detected presence status of the respective users. For example, as described above, the rendering module 44 may adjust rendering of the current record of the group play list responsive to detecting that an active one of the users associated with a current record is not present on the social network. Such a determination may be made shortly prior to rendering of the current record associated with the active one of the users and/or during rendering, and may affect delivery or rendering of the multimedia content record before initiating rendering thereof and/or during rendering. Note that, as used herein, reference to an active user refers to a user associated with a current record in the play list and reference to a current record may refer to a record that is about to be rendered (or rendered next) and/or to a record being rendered currently. In other words, in embodiments where the adjusting of the rendering occurs before beginning rendering a next record, the current record may be the record that is to be rendered next and in embodiments where adjusting rendering may occur during rendering of a record, the current record may further be the record that is currently being rendered. Stated differently, the phrase "current" and the phrase "active" are relative to the context of the adjusting of the rendering.

As noted above, the communications module 32 supports communications to and from the mobile terminal 10A, for example, the wireless communication connection 7 to the base station 5. Furthermore, in some embodiments of the present invention, the communication module 32 automatically establishes a communication connection between respective communication terminals associated with the active one of the users and a requesting one of the users responsive to a request received while rendering a multimedia content record associated with the current record (or slot) of the group play list. As will be further described herein, in various embodiments of the present invention, the communication connection may be a push to talk (PTT) link, a text message and/or other communication connection means. While the connection may be established responsive to the received request, it will be understood that the mobile terminal 10A may be configured to respond automatically, prior to receiving the request, responsive to detection of rendering of a multimedia content record associated with a user. For example, PTT may initiate a call to a first listed contact in a PTT list when a PPT button is selected as a request to initiate a call. In some embodiments, the mobile terminal 10A may have updated the PTT list to present the user associated with a currently rendering multimedia content record as the first listed contact before receiving the request to establish the connection, after which call set-up may proceed using ordinary PTT call setup capabilities of the mobile terminal 10A. It will be further understood that the mobile terminal 10A may separately automatically setup a distinct communication connection to obtain the multimedia content record from the associated user or other location independent of receipt of a request to establish a communication connection.

Although FIG. 1 illustrates an exemplary hardware/software architecture that may be used in mobile terminals and/or other electronic devices for management and playback of multimedia files, it will be understood that the present invention is not limited to such a configuration but is intended to encompass any configuration capable of carrying out operations described herein. For example, although the memory 34 is illustrated as separate from the controller 30, the memory 34 or portions thereof may be considered as a part of the controller 30. More generally, while particular functionalities are shown in particular blocks by way of illustration, functionalities of different blocks and/or portions thereof may be combined, divided, and/or eliminated. Moreover, the functionality of the hardware/software architecture of FIG. 1 may be implemented as a single processor system or a multi-processor system in accordance with various embodiments of the present invention.

Figure 2:
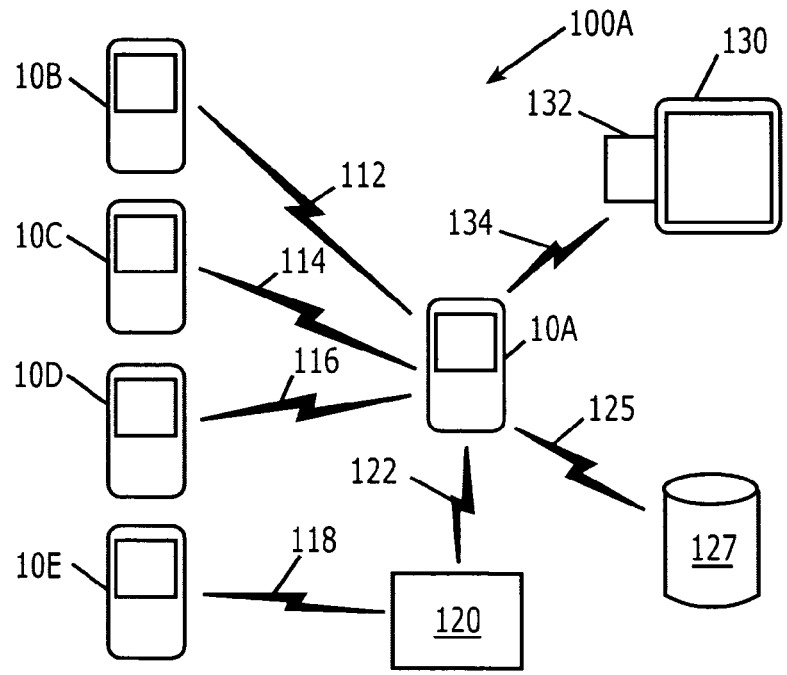
FIG. 2 is a schematic diagram of a multimedia file playback system according to some embodiments of the present invention including the mobile wireless communication terminal of FIG. 1.

Referring now to FIG. 2, a multimedia file playback system 100A associated with a user network, such as a computer based social network, according to some embodiments of the present invention is shown. The system 100A includes the mobile wireless communication terminal 10A (also referred to herein as the "host wireless communication terminal" or "host terminal"), a plurality of additional wireless communication terminals 10B, 10C, 10D, and 10E associated with users/members of the social network (also referred to herein as the "participant wireless communication terminals" or "participant terminals"), and a media center 130. As noted with reference to FIG. 1, while illustrated herein for purposes of explanation as wireless communication devices, the respective terminals need not be wireless and may be, for example, personal computers of the group members coupled over a wired and/or wireless connection link, such as the Internet, which may include both public and/or private network elements.

The terminals 10B-E may be configured as described above with regard to the terminal 10A. The terminals 10B-E each include a wireless communication module 32 and one or more of the generation module 40, presence detection module 42 and/or rendering module 44, which may be differently configured for the group member devices and the host device. In other words, the respective modules may be differently configured for each terminal 10A-E depending on the intended functionality of the device. According to some embodiments, all or some of the terminals 10B-E are mobile wireless communication terminals. According to some embodiments, all or some of the terminals 10A-E are handheld mobile wireless communication terminals.

In the embodiments illustrated in FIG. 2, the host terminal 10A is also communicatively coupled to the media center 130 to provide wireless multimedia file data signals via a wireless interface or link 134 to the communication module 132. The host terminal 10A can be connected to the media center 130 using a wireline or signal cable. As discussed above, the media center 130 may itself act as a host terminal that is configured to query potential group members and/or accept group member inputs and requests directly and/or indirectly from participant user mobile terminals. In fact, in some embodiments, no distinct media center 130 is provided and user terminals 10B-E create their own virtual network and exchange presence information and share multimedia content files as needed.

Once the connections are established between the host terminal 10A and the participant terminals 10B-E, each participant can send one or more participant multimedia file identification(s) designating a corresponding multimedia file stored on the participant's terminal 10B-E. In addition or in the alternative, the host terminal 10A can poll the participant terminals 10B-E to obtain a list of one or more available multimedia files stored on the participant terminals 10B-E. In some embodiments, multimedia files that the user of a participant terminal 10B-E wishes to identify for inclusion in a group play list may be stored in a designated folder or directory, such as a shared folder or directory. It may not be necessary for the user of the participant terminal 10B-E to designate files to be added to the group play list each time a connection is made to a host terminal 10A.

In some embodiments, with mixed media types, the host terminal 10A receives the participant multimedia file identifications from the participant terminals 10B-E and determines the type of multimedia file that each of the multimedia file identifications represents. This may be accomplished, for example, by inspecting a file type suffix for the file name. In some embodiments, the multimedia file identification includes an explicit indication of the type of multimedia file represented thereby. The host terminal 10A may create and maintain separate group play lists of these multimedia file identifications for each type of multimedia file that is accepted by the host terminal 10A. If the multimedia file identification represents a type of multimedia not supported by the host terminal 10A and/or the media center 130, the host terminal 10A may return an error message to the participant terminal 10B-E that submitted the multimedia file identification. The group play list represents multimedia files to be rendered by the host terminal 10A, the participant terminals 10B-E and/or at an associated media center 130. It will be understood that rendering of playlists need not be synchronized on all the participant terminals 10B-E. In other words, in some embodiments, some or all of the participants may be rendering different multimedia content at any given time.

A display of the group play list and/or a current entry in the group play list may be provided to the participant terminals 10B-E. Such a display 150 is shown, for example, in FIG. 3. In the illustrated embodiment, the display 150 includes a play list field 152 and control buttons 154 (e.g., soft keys). The control buttons 154 may not be displayed on some of the devices, where such devices are not to be provided control over rendering of the group play list, for the group or even for the local device. An exemplary audio file play list 156 is displayed in the play list field 152. The play list 156 includes a row-by-row series of multimedia file identifications 156A, each corresponding to a respective multimedia file and slot of the play list 156. In the case of an audio file, each multimedia file identification may includes an artist, a name, and a play time corresponding to the associated multimedia file, as well as an identification of the participant (group member) that has submitted the multimedia file identification and a current presence status of the identified participant. It will be appreciated that more, less and/or different information may be provided as well.

The rendering of the multimedia files represented by the multimedia file list 156 may be controlled using the control buttons 154, for example. For example, the "PLAY" and "STOP" buttons may be used to start and stop transmission of the multimedia files to the media center 130. The "MOVE" button may be used to manually change the order of the multimedia file identifications 156A in the play list 156 (i.e., to change the order in which the associated multimedia files will be played). The "DELETE" button may be used to delete a multimedia file identification 156A from the play list 156. The "DETAILS" button may be used to display additional information about a file identified by a multimedia file identification 156A. The "RANDOM MIX" button may be used to cause the host terminal 10A to execute playback of the multimedia files (e.g., send the multimedia files to the media center 138) in a random or other non-sequential order. However, it will be understood that the rendering of the multimedia content records will be automatically adjusted based on the presence status of a user associated with the current (i.e., ready to be rendered) multimedia content record.

The host terminal may simultaneously process both play lists, and may, for example, cause the media center 130 to sequentially display images from the image play list on a display while simultaneously causing the media center 130 to sequentially play audio files (e.g., songs) using a speaker system. In some embodiments, the host terminal 10A may process two play lists sequentially. For example, the host terminal 10A may alternate between playing audio files from an audio file play list and video files from a video file play list, so that video files, which typically include an audio track, may not be substantially played at the same time as an audio-only file. It will be understood, however, that the host terminal 10A may be configured to mix audio from an audio file with audio from another audio file or a video file as one file is ending and another is beginning (e.g., a cross-fade).

Thus, the play list represents multimedia files to be rendered. Separate play lists may be maintained at the host device for different types of multimedia files. For example, the host wireless terminal may maintain separate play lists for audio files, video files, and/or still image files. The separate play lists may be managed separately at the host wireless terminal, which may, for example, play multimedia files from the separate play lists simultaneously, sequentially, and/or a combination of simultaneously and sequentially. For example, the host wireless communication terminal may be configured to display still images on a video screen while audio files are played on a speaker. Similarly, the host wireless communication terminal may include or be coupled to a dedicated video screen for displaying video files, while still images are simultaneously displayed on a separate still image display screen. In order to reduce interference between audio in audio files and audio in video files, the host wireless communication terminal may be configured to sequentially play audio and/or video files from the respective video and audio play lists, while simultaneously displaying still images from the still image play list.

According to some embodiments, connections are established between the host wireless communication terminal and a plurality of participant wireless communication terminals, and the host wireless communication terminal receives a plurality of participant multimedia file identifications from the plurality of participant wireless communication terminals, adds each of the participant multimedia file identifications to the group play list, and retrieves the participant multimedia files from each of the respective participant wireless communication terminals for playback. According to some embodiments, communication between the host wireless communication terminal and the participant wireless communication terminal is accomplished via a direct point-to-point interface, such as a Bluetooth wireless RF connection. According to some embodiments, communication between the host wireless communication terminal and the participant wireless communication terminal is accomplished via an indirect interface, such as through a WLAN or other wireless network or cellular-based system.

Figure 4:
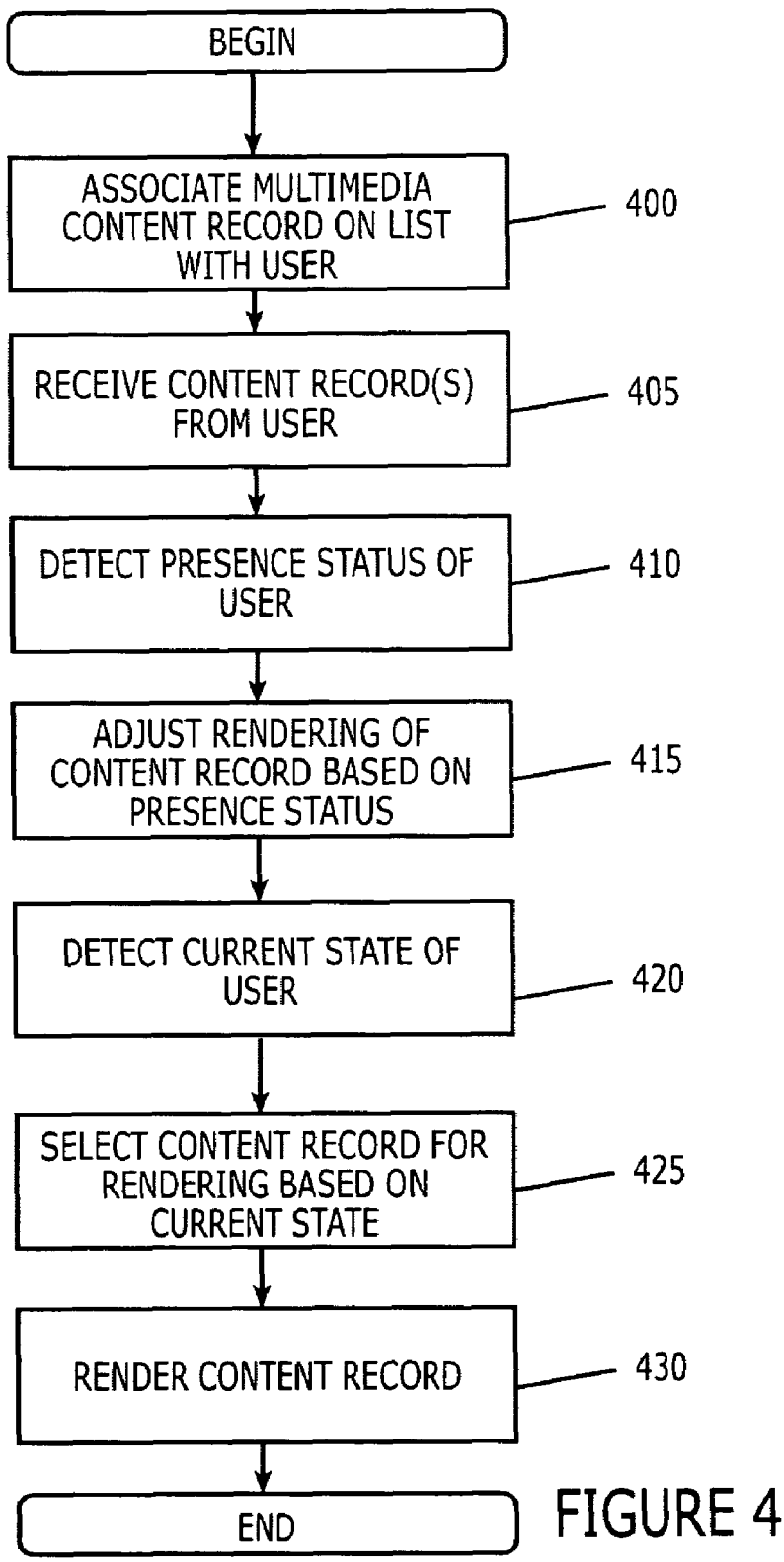
FIG. 4 is a flowchart illustrating methods in accordance with some embodiments of the present invention.

Methods for providing a group play list for a plurality of multimedia content records and rendering the group play list according to some embodiments of the present invention will now be described with reference to the flowchart illustrations of FIGS. 4 and 5. Referring first to the embodiments illustrated in FIG. 4, operations begin by associating respective ones of a plurality of users associated with a user network with corresponding ones of the multimedia content records on the group play list (block 400). The network may be a computer-based social network. The respective multimedia records may be associated with corresponding slots on the group play list and, furthermore, the slots on the group play list may be associated with corresponding ones of the users. As such, the association of a particular user with a multimedia content record may be based on placement of the multimedia content record or an identification thereof in a particular slot of the group play list, which slot may in turn be associated with a particular user to thereby associate the user with a multimedia content record.

An identification of the multimedia content record to be associated with a slot on the group play list may be received from the corresponding one of the users (block 405). The identification received from the user may be the multimedia content record itself. In some embodiments, the identification is a designation of a storage device and/or storage address from which the multimedia content record can be retrieved for rendering.

A presence status of the respective ones of the users associated with the user network is detected (block 410). Rendering of the multimedia content records on the group play list to the users associated with the network is automatically adjusted based on the detected presence status (block 415).

Embodiments of the present invention where a plurality of identifications of multimedia content records are associated with a single slot of the group play list will now be described with reference to blocks 420 and 425. For such embodiments, operations at block 405 may include receiving a plurality of identifications of multimedia content records to be associated with a single slot from the corresponding one of the users associated with a slot. Each of the plurality of received identifications has an associated user state. A current state associated with a respective one of the users associated with a single slot of the group play list is detected (block 420). For example, a user could be have different musical tastes when they are in a "happy" state than when they are in a "contemplative" state, and the current state detected at block 420 may distinguish whether the user is currently happy or contemplative. The detection of the current state may be performed concurrently with or just prior to adjusting the rendering as described at block 415 and may, thus, be associated with a current record and/or active user as discussed previously with reference to FIG. 1. However, the current state determination of block 420 may also be determined at a different time from the determinations discussed above regarding presence status relative to an active user for a current record (slot) in the group play list.

One of the plurality of identifications received for the single slot is selected as corresponding to the multimedia content record to be rendered for the single slot based on a comparison of a detected current state of a respective one of the users and an associated user state of the plurality of identifications (block 425). The selected content record is rendered (block 430).

Figure 5:
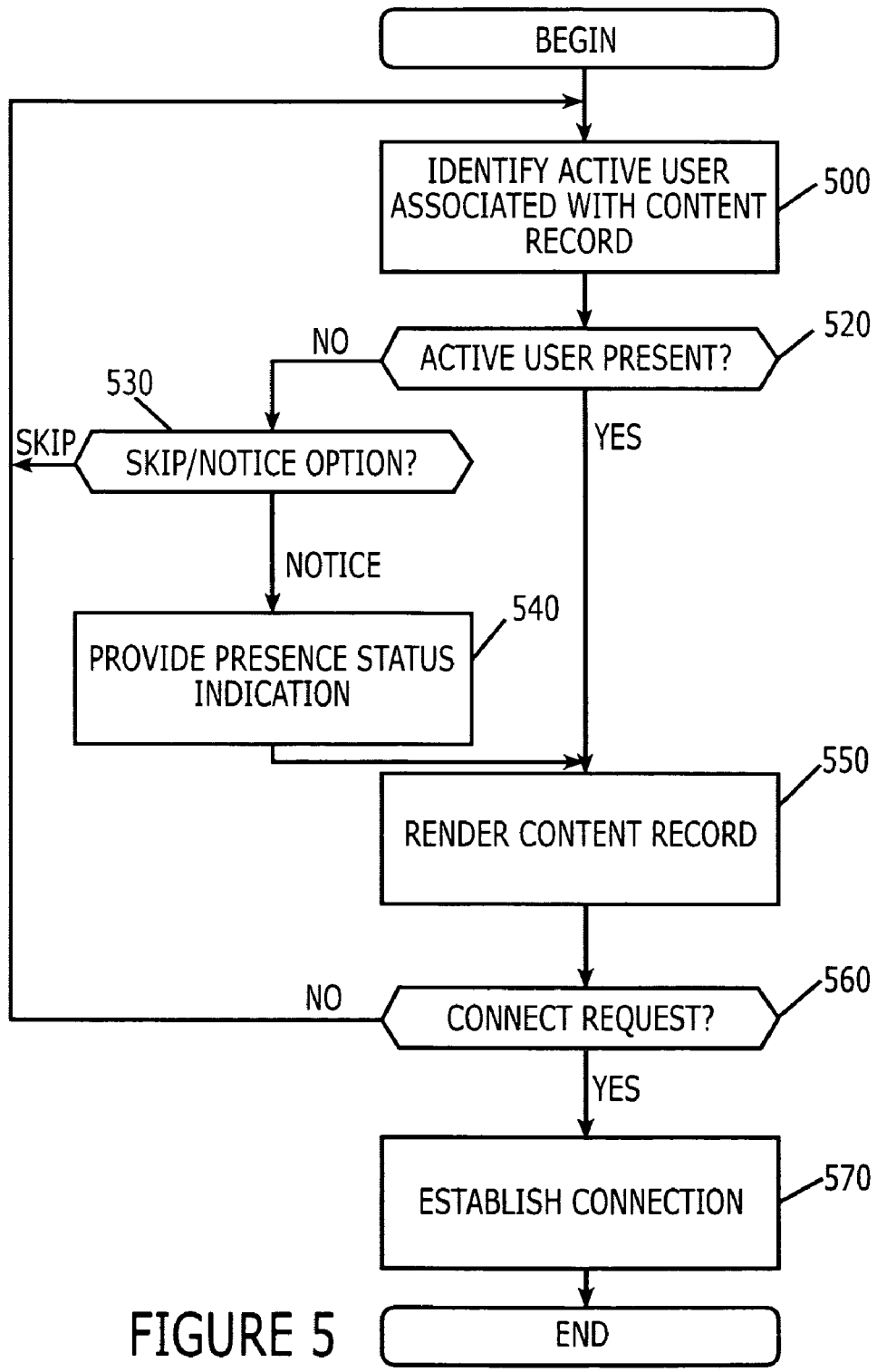
FIG. 5 is a flowchart illustrating methods in accordance with further embodiments of the present invention.

Referring now to the embodiments illustrated in FIG. 5, operations begin by identifying one of the users associated with the social network (active user) as corresponding with one of the multimedia content records on the group play list (current record) (block 500). A presence status of the active user is detected (block 520). When the active user is detected as present (block 520), the content record is rendered (block 550). When it is detected that the active user is not present on the social network (block 520), and the skip rendering option feature is detected (block 530), rendering of the content record is bypassed and operations return to identifying a next active user for the following record at block 500. In other words, when it is detected that the active user is not present on the social network, automatically adjusting rendering may include skipping rendering the active user's corresponding multimedia content record responsive to the determination that the active user is not present on the network.

In some embodiments, when the active user is not present (block 520) and the notice option has been selected (block 530), adjusting rendering includes including an indication of the presence status of the corresponding one of the users (the active user) having a presence status indicating that the respective user is not present on the user network while rendering the respective multimedia content record associated with the not-present user (block 540). For example, a status indication may be provided as shown in the play list of FIG. 3. The content record may then be provided concurrently and/or after providing the status indication (block 550).

Operations for further embodiments of the present invention will now be described with reference to block 560 and 570. As illustrated in FIG. 5, a request may be received from a requesting one of the users who are group members of the user network to communicate with the active user corresponding to a multimedia content record that is currently being rendered (block 560). When such a request is received (block 560), a communication connection between respective ones of the communication terminals associated with an active user and the requesting user is automatically established responsive to the received request (block 570). For example, the communication terminals associated with a requesting user and the active user may be wireless mobile terminals, the communication connection may be a push to talk (PTT) communication connection and the request received at block 560 may be received by detecting selection of a PTT feature of the requesting user. In such embodiments, establishing a communication connection at block 570 may include prioritizing an identification of the active user in a contact list associated with a PTT feature. For example, prioritizing the identification may include placing the identification at the top of the contact list, which top entry may be the number selected for establishing the connection responsive to selection of the PTT feature. However, it will be understood that, in some embodiments, placing of the identification at the top of the contact list may have occurred responsive to rendering of the multimedia content and before receipt of the request to establish a connection at block 560.

Thus, in some embodiments of the present invention, support is provided allowing linkage and/or communication with a group member when their contribution to the group play list is currently playing. For example, if a user "Ben" is listening to the group play list and the "Usher" song that was added to the play list by "Matt" is played, then the rendering device (which may be a communication terminal associated with user "Ben" and/or a host device as described previously) may facilitate a call from "Ben" to "Matt." For example, in this condition, a long press on the PTT button of Ben's communication device may initiate a call to the group member (Matt) whom with the content in the group play list is associated.

In further embodiments, the communication connection established at block 570 is a text message transmission. Automatically establishing the communication may include prioritizing an identification of the active user in a contact list associated with a text message feature of the requesting user's communication terminal to facilitate automatic transmission of a text message from a requesting user to the active user. The text message may further be pre-addressed and/or pre-populated with message content specified by the sending user.

In the drawings and specification, there have been disclosed exemplary embodiments of the invention. Although specific terms are employed, they are used in a generic and descriptive sense only and not for purposes of limitation, the scope of the invention being defined by the following claims.

That which is claimed is:

1. A method for providing a group play list for a plurality of multimedia content records, comprising:
associating respective ones of a plurality of users associated with a user network with corresponding ones of the multimedia content records on the group play list;
detecting a presence status of the respective ones of the users associated with the user network; and
automatically adjusting rendering of the multimedia content records on the group play list to the users associated with the network based on the detected presence status,
wherein automatically adjusting rendering comprises skipping rendering of a multimedia content record on the group play list associated with one of the respective ones of the users having a presence status indicating the one of the respective ones of the users is not present on the user network.

2. The method of claim 1, wherein the user network comprises a computer based social network.

3. The method of claim 1, wherein automatically adjusting rendering comprises including an indication of the presence status of one of the respective ones of the users having a presence status indicating the one of the respective ones of the users is not present on the user network while rendering a multimedia content record on the group play list associated with the one of the respective ones of the users having a presence status indicating the one of the respective ones of the users is not present on the user network.

4. The method of claim 1, wherein the users are associated with respective communication terminals and wherein the method further comprises:
identifying a respective one of the users associated with one of the multimedia content records that is currently being rendered as an active user;
receiving a request from a requesting one of the users to communicate with the active user; and
automatically establishing a communication connection between respective ones of the communication terminals associated with the active user and the requesting user responsive to the received request.

5. The method of claim 4, wherein the communication terminals associated with the requesting user and the active user comprise wireless mobile terminals and wherein the communication connection comprises a push to talk (PTT) communication connection and wherein receiving the requesting comprises detecting selection of a PTT feature of the requesting user.

6. The method of claim 5, wherein automatically establishing the communication connection includes prioritizing an identification of the active user in a contact list associated with the PTT feature.

7. The method of claim 6, wherein prioritizing the identification comprises placing the identification at a top of the contact list.

8. The method of claim 4, wherein the communication terminals associated with the requesting user and the active user comprise wireless mobile terminals and wherein the communication connection comprises a text message transmission and wherein automatically establishing the communication connection includes prioritizing an identification of the active user in a contact list associated with a text message feature of the communication terminal of the requesting user.

9. The method of claim 4, wherein receiving a request is preceded by configuring the communication terminal of the requesting user to communicate with the communication terminal of the active user responsive to identifying the active user.

10. The method of claim 9, wherein the communication terminals associated with the requesting user and the active user comprise wireless mobile terminals and wherein the communication connection comprises a push to talk (PTT) communication connection and wherein receiving the requesting comprises detecting selection of a PTT feature of the requesting user and wherein configuring the communication terminal of the requesting user comprises prioritizing an identification of the active user in a contact list associated with the PTT feature.

11. The method of claim 10 wherein prioritizing the identification comprises placing the identification at a top of the contact list.

12. The method of claim 1, wherein ones of the multimedia content records are associated with respective slots on the group play list and wherein the slots on the group play list are associated with corresponding ones of the users.

13. The method of claim 12, wherein associating respective ones of the users comprises receiving an identification of the multimedia content record to be associated with respective slots on the group play list from the corresponding ones of the users.

14. The method of claim 13, wherein receiving an identification comprises receiving the multimedia content record.

15. The method of claim 13, wherein receiving an identification comprises receiving a designation of a storage device and/or storage address from which the multimedia content record can be retrieved for rendering.

16. The method of claim 13, wherein associating respective ones of the users further comprises receiving a plurality of identifications of multimedia content records to be associated with a single slot of the group play list from the corresponding one of the users, each of the plurality of identifications having an associated user state and wherein automatically adjusting rendering further comprises:
 detecting a current state associated with a respective one of the users associated with the single slot of the group play list; and
 selecting one of the plurality of the identifications received for the single slot as corresponding to the multimedia content record to be rendered for the single slot based on a comparison of the detected current state of the respective one of the users and the associated user state of the plurality of identifications.

17. A communication system configured to carry out the method of claim 1.

18. A computer program product for providing a group play list for a plurality of multimedia content records, the computer program product comprising computer program code embodied in a computer readable medium, the computer program code comprising program code configured to carry out the method of claim 1.

19. A system for rendering a group play list including a plurality of multimedia content records, the group play list being associated with a computer based social network, the system comprising:
 a generation module that generates the group play list including associating respective ones of a plurality of users associated with the computer based social network with corresponding ones of the multimedia content records on the group play list;
 a presence detection module that detects a presence status of the respective ones of the users on the computer based social network; and
 a rendering module that renders the multimedia content records on the group play list to the users associated with the computer based social network based on the detected presence status of the respective users, including skipping rendering of a current record of the group play list responsive to detecting that an active one of the users associated with the current record is not present on the computer based social network.

20. The system of claim 19, further comprising a communication module that automatically establishes a communication connection between respective communication terminals associated with the active one of the users and a requesting one of the users responsive to a request received while rendering a multimedia content record associated with the current record.

* * * * *